United States Patent
Mahfouz

(10) Patent No.: US 10,441,362 B2
(45) Date of Patent: Oct. 15, 2019

(54) FEMORAL BASE PLATE THA

(71) Applicant: Mohamed R. Mahfouz, Knoxville, TN (US)

(72) Inventor: Mohamed R. Mahfouz, Knoxville, TN (US)

(73) Assignee: TechMah Medical, LLC, Knoxville, TN (US)

( * ) Notice: Subject to any disclaimer, the term of this patent is extended or adjusted under 35 U.S.C. 154(b) by 130 days.

(21) Appl. No.: 15/663,934

(22) Filed: Jul. 31, 2017

(65) Prior Publication Data

US 2018/0049807 A1 Feb. 22, 2018

Related U.S. Application Data

(63) Continuation of application No. 15/381,031, filed on Dec. 15, 2016, now abandoned.

(60) Provisional application No. 62/267,370, filed on Dec. 15, 2015.

(51) Int. Cl.
| | | |
|---|---|---|
| *A61B 17/80* | (2006.01) | |
| *A61F 2/46* | (2006.01) | |
| *A61B 34/10* | (2016.01) | |
| *A61F 2/38* | (2006.01) | |

(Continued)

(52) U.S. Cl.
CPC .............. *A61B 34/10* (2016.02); *A61B 17/80* (2013.01); *A61B 17/808* (2013.01); *A61B 17/8061* (2013.01); *A61F 2/3859* (2013.01); *A61F 2/4607* (2013.01); *A61B 2034/104* (2016.02); *A61B 2034/105* (2016.02); *A61B 2034/108* (2016.02); *A61B 2034/2048* (2016.02); *A61F 2002/30945* (2013.01);
(Continued)

(58) Field of Classification Search
None
See application file for complete search history.

(56) References Cited

U.S. PATENT DOCUMENTS

| | | |
|---|---|---|
| 2001/0011172 A1 | 8/2001 | Orbay et al. |
| 2006/0004361 A1 | 1/2006 | Hayeck et al. |
| 2007/0088360 A1 | 4/2007 | Orbay et al. |

(Continued)

FOREIGN PATENT DOCUMENTS

| | | |
|---|---|---|
| WO | PCT/US16/067060 | 3/2017 |
| WO | WO2017106580 A1 | 6/2017 |
| WO | PCT/US16/067060 | 6/2018 |

*Primary Examiner* — David H Willse
(74) *Attorney, Agent, or Firm* — Dorton & Willis, LLP; Ryan Willis

(57) ABSTRACT

A method of creating a mass-customized femoral bone base plate comprising: (i) establishing anatomical landmarks across a plurality of bone models of a statistical atlas; (ii) establishing instrument landmarks across the plurality of bone models of the statistical atlas; (iii) establishing definitions for a reference plane calculation across the plurality of bone models of the statistical atlas, where the reference plane represents a boundary of a prosthetic implant; (iv) establishing an attachment site for a mass-customized femoral bone base plate using the anatomical landmarks, the instrument landmarks, and the reference plane; and, (v) fabricating the mass-customized femoral bone base plate configured to be attached to a femur, where the attachment sites of the mass-customized femoral bone base plate are predetermined to avoid impingement with the prosthetic implant when implanted.

20 Claims, 16 Drawing Sheets

(51) Int. Cl.
*A61F 2/30* (2006.01)
*A61B 34/20* (2016.01)

(52) U.S. Cl.
CPC ... *A61F 2002/4633* (2013.01); *Y10S 623/908* (2013.01); *Y10S 623/911* (2013.01)

(56) References Cited

U.S. PATENT DOCUMENTS

| | | |
|---|---|---|
| 2010/0174285 A1 | 7/2010 | Probe |
| 2012/0106819 A1* | 5/2012 | Fernandez Oca ...... A61B 34/10 382/132 |
| 2015/0051650 A1* | 2/2015 | Verstreken ........... A61B 17/151 606/281 |

* cited by examiner

|  | S1 | S2 | S3 |
|---|---|---|---|
| Mean | 4.107559 | 4.322052 | 6.636619 |
| Standard Deviation | 2.407339 | 2.42296 | 2.327729 |
| Minimum | 0.098128 | 0.017434 | 2.85353 |
| Maximum | 13.7247 | 12.9627 | 14.3009 |

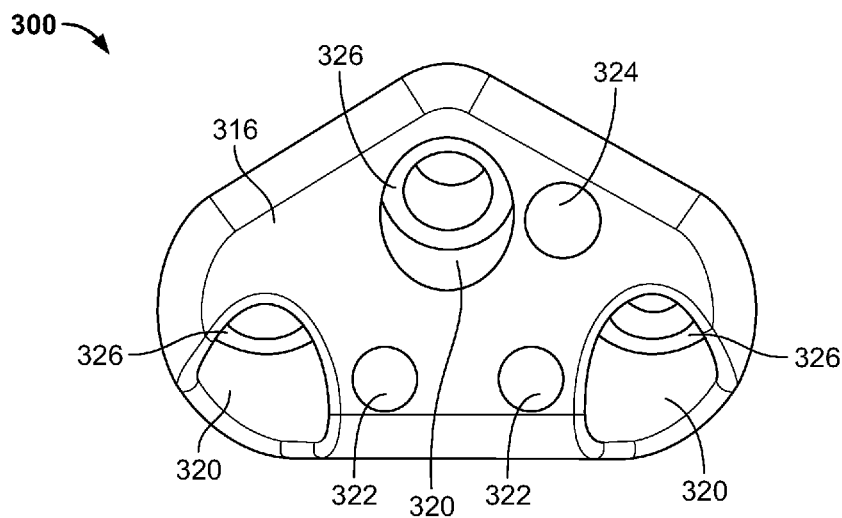
FIG. 26
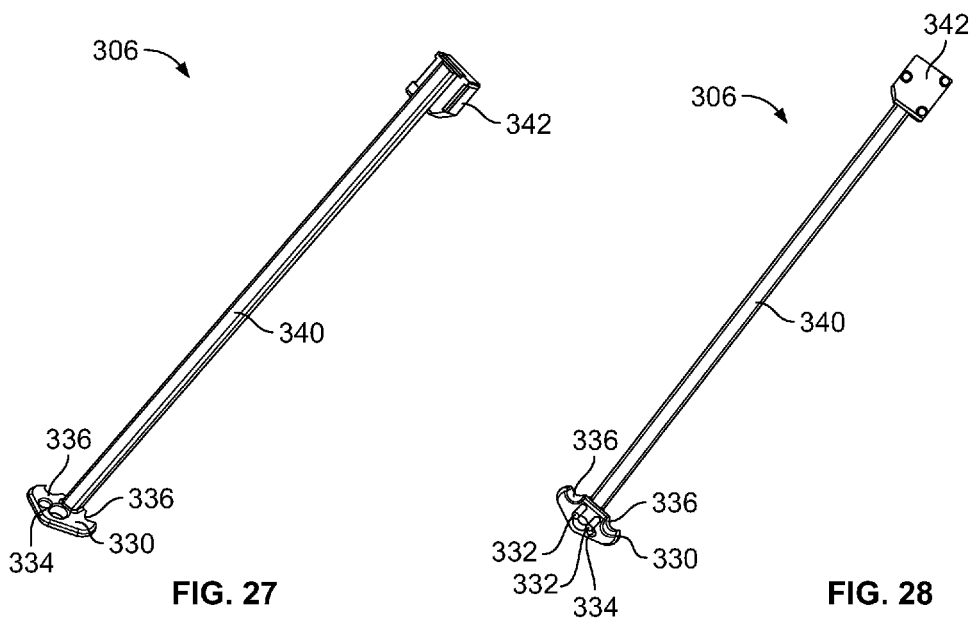
FIG. 27
FIG. 28

FEMORAL BASE PLATE THA

CROSS REFERENCE TO RELATED APPLICATIONS

The present application is a continuation of U.S. Nonprovisional patent application Ser. No. 15/381,031, titled "FEMORAL BASE PLATE THA," filed Dec. 15, 2016, and claims the benefit U.S. Provisional Patent Application Ser. No. 62/267,370, titled "FEMORAL BASE PLATE THA," filed Dec. 15, 2015, the disclosure of each of which is incorporated herein by reference.

INTRODUCTION TO THE INVENTION

The present disclosure is directed to optimization of shape, placement, and screw locations for attachment of a femoral base plate that may be used with a posterior approach for total hip arthroplasty using a surgical navigation system including inertial measurement units. As will be discussed in more detail hereafter, the shape of the femoral base plate is taken from the mean surface curvature of a statistical atlas of femoral bones at a defined base plate attachment site. This base plate attachment site may be dependent on screw length and locations, so that when placed correctly the attachment screws do not impinge on the proposed rasp and stem components.

It should be noted that Patent Cooperation Treaty application PCT/US14/69411, filed Dec. 9, 2014 is hereby incorporated by reference. Portions of the foregoing application are appended hereto as Appendix A.

BRIEF DESCRIPTION OF THE DRAWINGS

FIG. 26 is a top view of the exemplary femoral base plate of FIG. 24.

FIG. 27 is a right side view of a second exemplary stem in accordance with the instant disclosure.

FIG. 28 is an elevated perspective view of the stem of FIG. 27.

DETAILED DESCRIPTION

The exemplary embodiments of the present disclosure are described and illustrated below to encompass various aspects of orthopedics including surgical navigation aids, surgical navigation, and mass customized instruments to use with surgical navigation. Of course, it will be apparent to those of ordinary skill in the art that the embodiments discussed below are exemplary in nature and may be reconfigured without departing from the scope and spirit of the present invention. However, for clarity and precision, the exemplary embodiments as discussed below may include optional steps, methods, and features that one of ordinary skill should recognize as not being a requisite to fall within the scope of the present invention.

Figure 1:
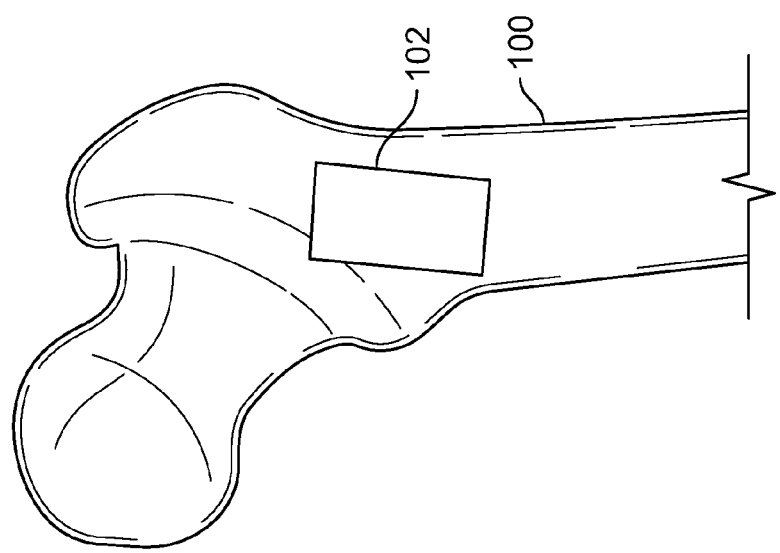
FIG. 1 is a diagram depicting a proximal portion of a femur that includes the femoral ball and a proposed attachment site for a bone base plate in accordance with the instant disclosure.

As depicted in FIG. 1, a plurality of femoral bone models 100 (that may be in excess of 150 models, though could certainly be less) as part of a statistical atlas (where the bone models include intramedullary canal 110 models) is utilized to identify a general attachment site 102 (i.e., landmarking) for a femoral bone base plate using bone model geometry. In other words, this attachment site 102 for the femoral bone base plate is delineated on each femoral bone model 100 of the atlas in generally the same bone model area across two or more of the bone models of the atlas. Based upon this location propagation, the atlas includes local geometry data as to the dimensions (including surface profile) of the surface of each bone model where the femoral bone base plate attachment site 102 overlaps or is otherwise bounded by. In this fashion, the bone contacting surface of the femoral bone base plate may be established by averaging or otherwise using the dimensions of the bone model at the attachment site 102 locations post propagating the attachment site across the statistical atlas.

The following series of steps are exemplary in nature and elaborate on an exemplary femoral bone base plate attachment site 102 (landmarking) methodology in the context of establishing anatomical landmarks and references across the bone models 100 of the statistical atlas utilized. Though not required, the following steps may be performed on each of the bone models 100 utilized as part of the statistical atlas. In exemplary fashion, each bone model 100 utilized as part of the statistical atlas is evaluated to: (1) compute the tip of the femoral lesser trochanter point (LT); (2) compute the plane marking the edge of the lesser trochanter, tangent to the femoral shaft (LTEP); (3) compute the femoral overall anatomical axis (AA); (4) compute projection of the lesser trochanter point on the femoral overall anatomical axis (PLTPAA); (5) compute projection of the lesser trochanter point on the plane marking the edge of the lesser trochanter (PLTPLTEP); (6) compute medial-lateral direction as a vector between PLTPAA and LT; (7) compute anterior-posterior direction as a cross product of the femoral overall anatomical axis and medial-lateral direction; and, (8) compute superior inferior direction as the femoral overall anatomical axis direction.

Figure 2:
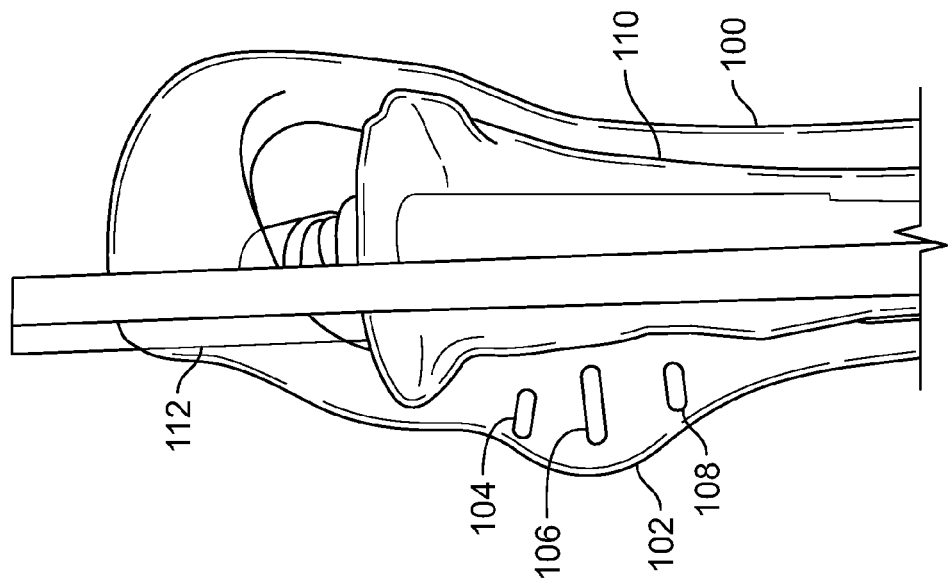
FIG. 2 is a partially resected femoral bone model showing placement of three surgical screws and the trajectory and position relative to the intramedullary canal of the femur and the boundary of the femoral stem of an orthopedic implant positioned within the intramedullary canal.

With respect to FIG. 2, the following series of steps are exemplary in nature and elaborate on an exemplary femoral bone base plate attachment site 102 (landmarking) methodology in the context of establishing instrument landmarks and directions across the bone models 100 of the statistical atlas utilized. By way of example, screw locations for securing the femoral bone base plate to the femur and directions the screws 104-108 will take relative to the bone are derived from a series of placement steps relative to appropriate anatomical landmarks. In this fashion, the screw locations and directions are repeatable per bone model 100 of the statistical atlas and, accordingly, allows for common analysis across the statistical atlas population utilized. Though not required, the following steps may be performed on each of the bone models utilized as part of the statistical atlas. In exemplary fashion, each bone model 100 utilized as part of the statistical atlas is evaluated to: (1) compute the shifted lesser trochanter point as PLTPLTEP is shifted 1 millimeter in the medial-lateral direction (Shifted_PLTPLTEP); (2) compute the location Screw #1 (S1) 106 as the intersection of the line pointing along the anterior-posterior direction and passing through Shifted_PLTPLTEP and the femoral bone model; (3) compute the midpoint between Screw #2 104 and Screw #3 108 as the location of Screw #1 (S1) 106 is shifted 5 millimeters in the medial-lateral direction (MP_S2_S3); (4) compute the location of Screw #2 (S2) 108 as the closest point on the femoral bone model to the MP_S2_S3 point shifted 1 millimeter proximally in the direction of the anatomical axis; (5) compute the point of Screw #3 (S3) 104 as the closest point on the femoral bone model to the MP_S2_S3 point shifted 1 millimeter distally in the direction of the anatomical axis; (6) compute the femoral plate plane as the plane containing the screw locations for all three Screws (Screw #1 (S1) 106, Screw #2 (S2) 108, Screw #3 (S3) 104); (7) compute the direction of Screw #1 (S1) 106 as the direction normal to the femoral plate plane; and, (8) compute the direction of Screw #2 (S2) 108 and Screw #3 (S3) 104 to be normal to the femoral plate plane plate plane after rotating the femoral plate plane 20 degrees medially around the axis connecting the location of Screw #2 (S2) 108 and the location of Screw #3 (S3) 104.

Figure 4:
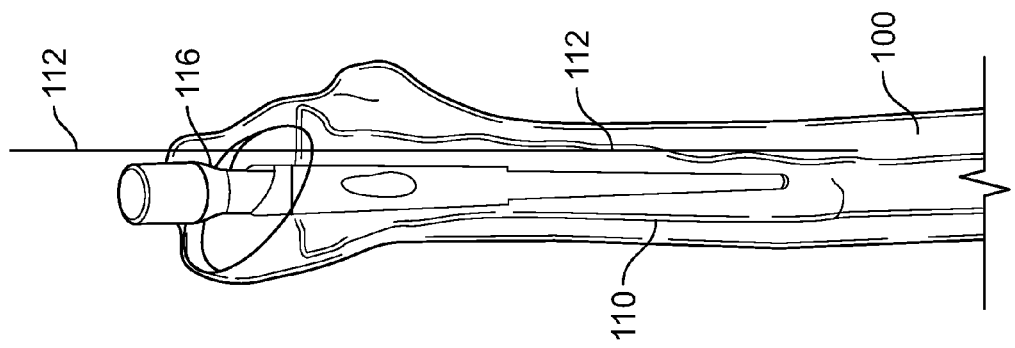
FIG. 4 is the partially resected femoral bone model of FIG. 3 shown with the reference plane in position.
Figure 3:
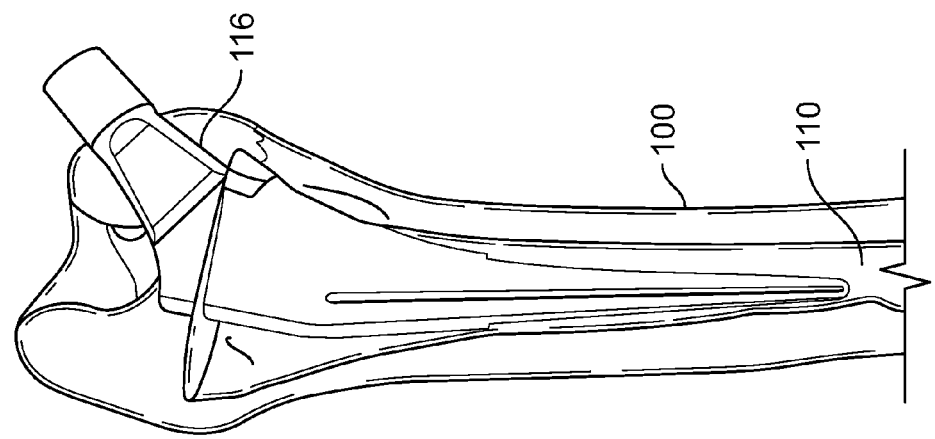
FIG. 3 is a partially resected femoral bone model showing an intramedullary canal of the femur and the boundary of the femoral stem of an orthopedic implant positioned within the intramedullary canal.

With respect to FIGS. 3 and 4, the following series of steps are exemplary in nature and elaborate on an exemplary femoral bone base plate attachment site (landmarking) methodology in the context of establishing definitions for reference plane 112 calculations across the bone models of the statistical atlas utilized. The reference plane 112 is a plane that represents the significant boundary of the implanted component with respect to the bone in question, such as a femur. In exemplary form, the reference plane 112 is defined so that it represents the expected component placement (femoral implant stem) plus a significant margin of placement error to provide a conservative estimate of the outer volume boundary of the orthopedic implant component with respect to the bone. For purposes of explanation and assessment, any fixation screw 104-108 is identified as having a potential impingement if its placement would result in any portion of the screw passing through the boundary delineated by the reference plane 112. Though not required, the following steps may be performed on each of the bone models 100 utilized as part of the statistical atlas. In exemplary fashion, each bone model 100 utilized as part of the statistical atlas is evaluated to: (1) define a reference plane 112 normal to the proximal anatomical axis and the neck axis and passing through the anatomical axis point (ref_temp_plane); (2) compute the reference plane 112 as a plane rotated 5 degrees (error boundary of the system) and translated 7 millimeters (determined by using a 5 millimeter measurement of an average rasp width and 2 millimeter buffer or safe zone built in); (3) compute the distance between the terminal end of each of the three screws (S1, S2, S3) 104-108 and the reference plane 112, as well as noting that any screw passing through the reference plane is identified as having impingement. For purposes of the foregoing, the screw length was set at 13 millimeters and presumed to be flush with the outer surface of the bone model post installation/fixation. And FIGS. 3 and 4 depict a femoral stem prosthetic 116 being positioned partially within the intramedullary canal 110.

Figures 5, 6:
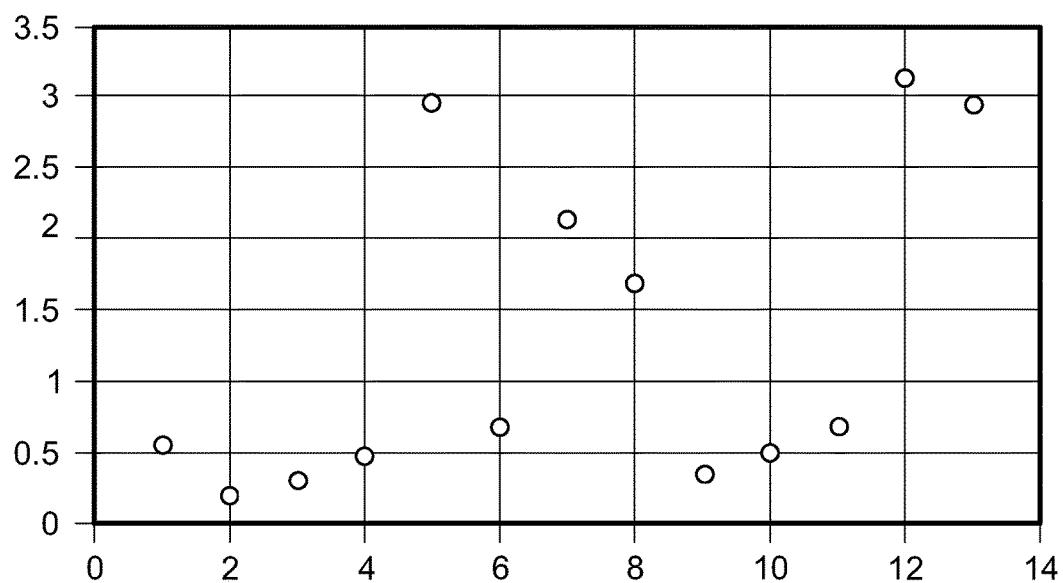
FIG. 5 is a table showing the mean, standard deviation, minimum, and maximum distances respective screw distal ends were with respect to the reference plane using the modeling and computations in accordance with the instant disclosure.
FIG. 6 is a chart depicting 13 impingement circumstances where the first screw pierced the reference plane and how far the first screws extended beyond the reference plane once pierced.
Figure 7:
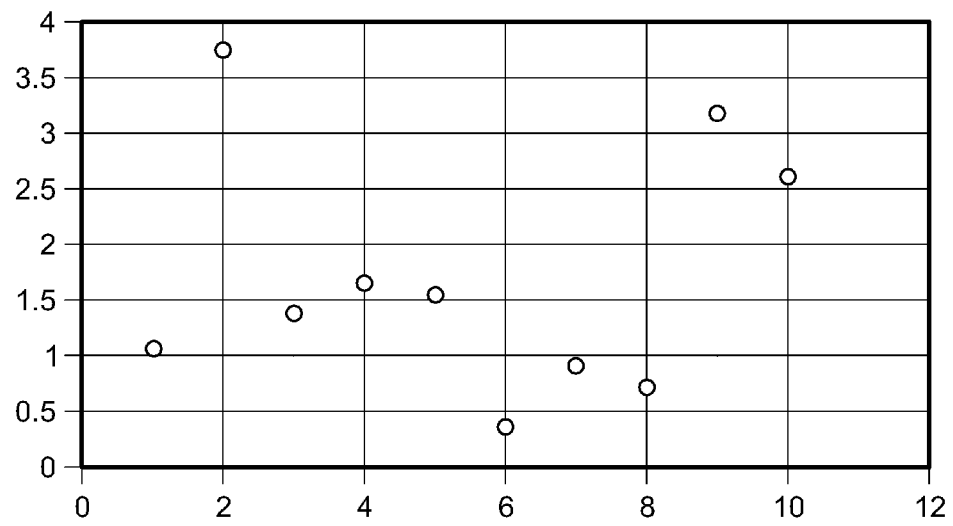
FIG. 7 is a chart depicting 10 impingement circumstances where the second screw pierced the reference plane and how far the second screws extended beyond the reference plane once pierced.
Figure 8:
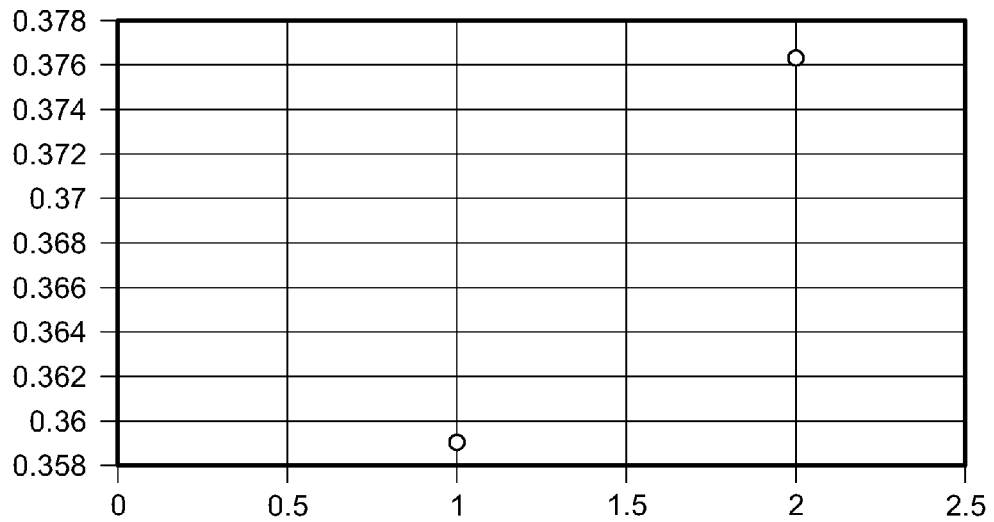
FIG. 8 is a chart depicting 2 impingement circumstances where the third screw pierced the reference plane and how far the third screws extended beyond the reference plane once pierced.

Referring to FIGS. 5-8, evaluation of the computations and determinations across all of the bone models 100 utilized as part of the statistical atlas was carried out. As depicted in FIG. 5, a chart provides the mean, standard deviation, minimum, and maximum dimensions in millimeters for the distance from the terminal end of a respective screw 104-108 to the reference plane. The foregoing analysis was performed for 150 atlas bone models. As part of the computations and determinations, 116 of 150 bone models had no instances of impingement between any of the three screws and the reference plane. In the remaining 34 cases, 15 cases had impingement of the screws 104-108 with respect to the reference plane 112. It is worth noting that the reference plane 112 is defined based on femoral geometry landmarks, which in some cases might not correlate to the boundaries of the segmented intramedullary canal model.

The results of the computations and determinations across all of the bone models 100 utilized as part of the statistical atlas resulted in an attachment site 102 and shape of a femoral bone base plate surface configured to be adjacent the bone surface that is mass customized to fit across a range of patient femur sizes for implant sizes that vary.

With the shape of the exemplary femoral bone base plate surface and attachment site established, one may fabricate the femoral bone base plate 200 and use the same as part of a total hip arthroplasty procedure in order to register one or more inertial measurement units 202 with respect to a patient's femur 204 as part of a surgical navigation endeavor. As will be discussed in greater detail hereafter, the exemplary femoral bone base plate 200 works with one or more inertial measurement units 202 and a stem 206 to comprise a bone reference assembly 210. In this fashion, the inertial measurement unit (IMU) 202 is fastened to a bone 204 (in exemplary form, a femur) in a fixed position and acts as a reference IMU, where this fixed position is retained throughout the surgical procedure (which may include final implant placement within the intramedullary canal of the femur). Reference is had to Appendix A, included herewith, that describes in more detail the interaction between reference IMU and a second IMU mounted to a surgical tool or surgical implant as part of surgical navigation in order to provide information regarding the relative positions of bone, implant, and surgical tools when direct line of sight to one or more of these objects may be absent.

Figure 10:
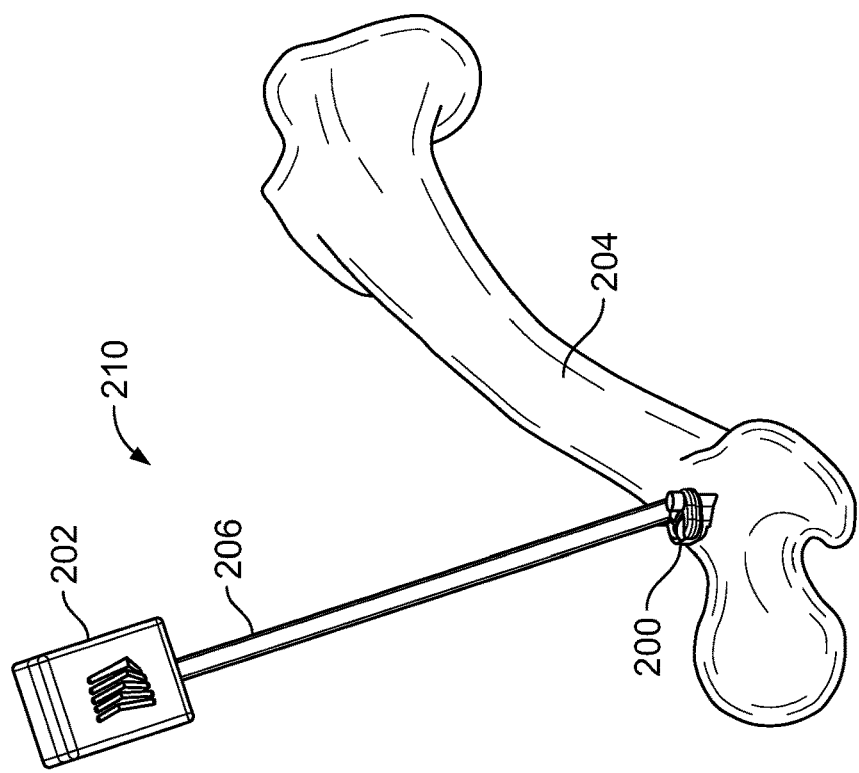
FIG. 10 is a diagram showing placement of the first exemplary bone reference assembly on an anterior portion of a femur.
Figure 9:
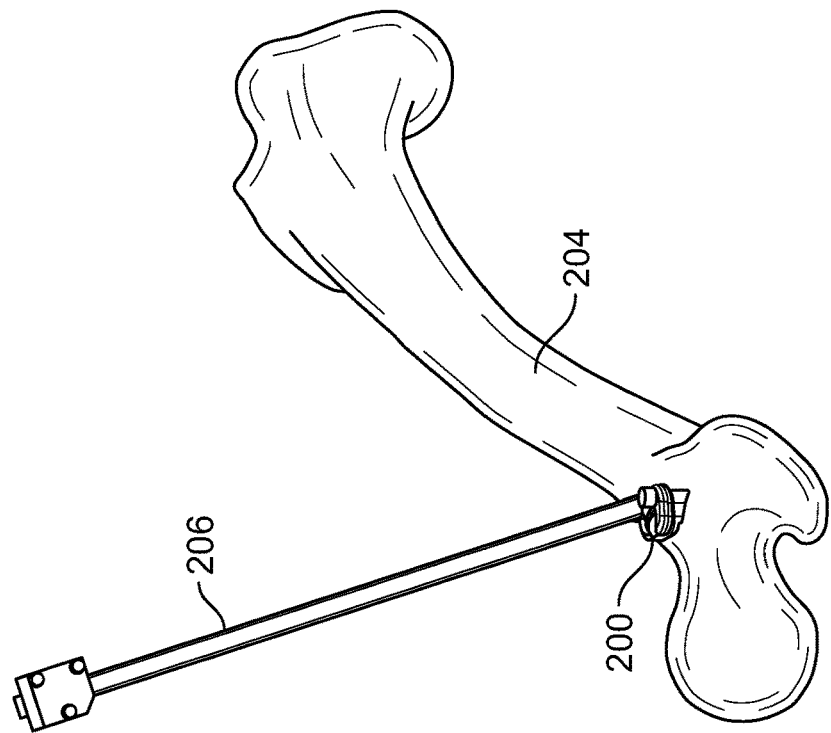
FIG. 9 is a diagram showing placement of the first exemplary bone reference assembly (without the IMU) on an anterior portion of a femur.

As depicted in FIG. 10, an exemplary bone reference assembly 210 for a femur 204 comprises an inertial measurement unit 202, a stem 206, and a bone base plate 200 (in exemplary form, a femoral bone base plate). Though not necessarily limited to applications on an attachment site on the anterior region of the femur, the foregoing exemplary embodiment may be referred to as an exemplary anterior bone reference assembly 210.

Figure 11:
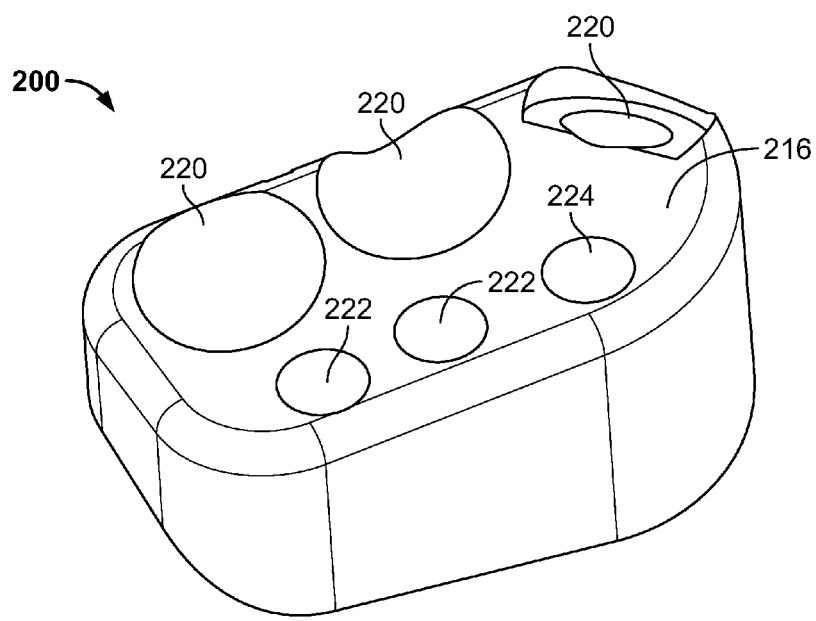
FIG. 11 is a top, elevated perspective view of an exemplary femoral bone base plate in accordance with the instant disclosure.
Figure 12:
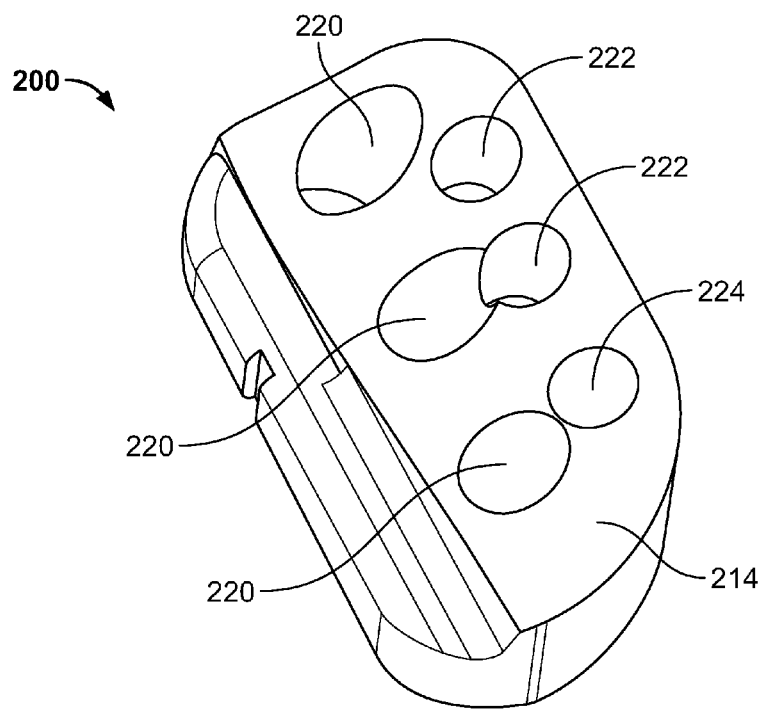
FIG. 12 is a bottom, subverted perspective view of the exemplary femoral base plate of FIG. 11.
Figure 13:
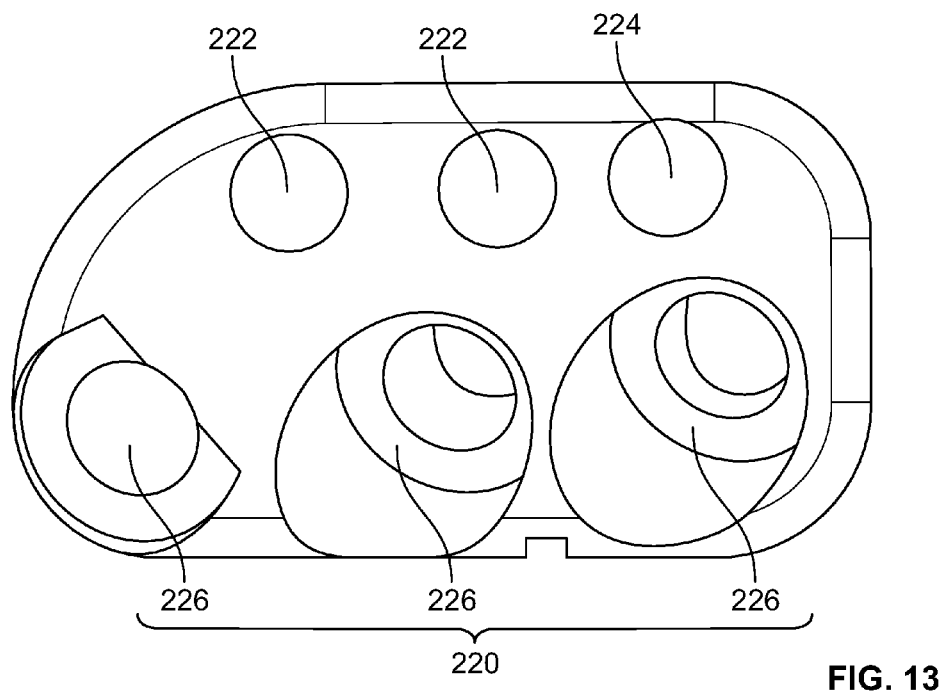
FIG. 13 is a top view of the exemplary femoral base plate of FIG. 11.
Figures 14, 15:
FIG. 14 is a right side view of an exemplary stem in accordance with the instant disclosure.
FIG. 15 is an elevated perspective view of the stem of FIG. 14.
Figure 16:
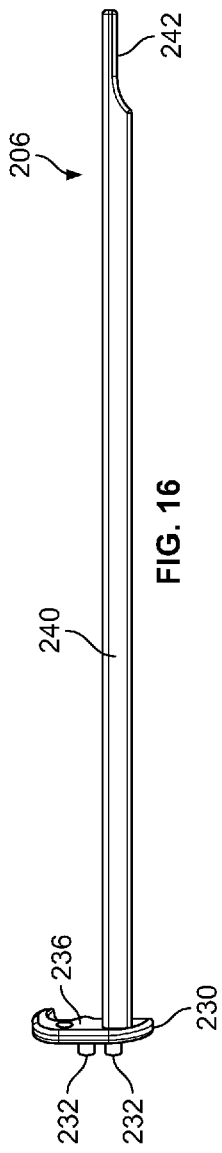
FIG. 16 is a profile view of an alternate exemplary stem.
Figure 17:
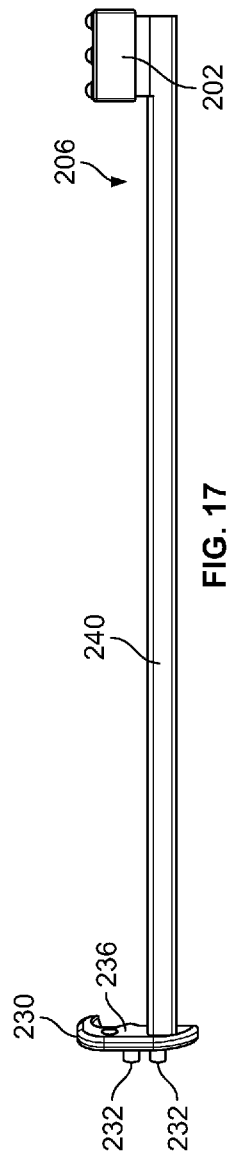
FIG. 17 is a profile view of the exemplary stem of FIG. 14.
Figure 18:
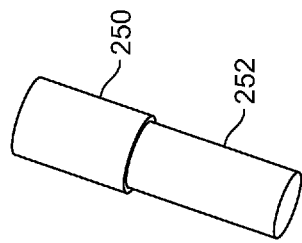
FIG. 18 is an elevated perspective view of a fastener in accordance with the instant disclosure.
Figure 19:
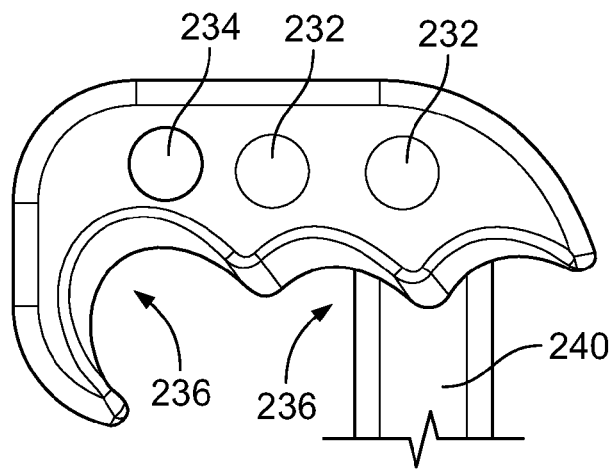
FIG. 19 is a bottom view of a portion of the stem of FIG. 14.

As depicted in more detail in FIGS. 11-13, the shape of the exemplary femoral bone base plate 200 and fixation locations are established mathematically and confirmed using bone models 100 from a statistical atlas. The exemplary femoral bone base plate 200 includes a distal, bone contacting surface 214 having a topography that generally matches and mates with the topography of an anterior portion of a femur that is exposed as part of a total hip arthroplasty procedure. Opposite the bone contacting surface 214 is a stem interfacing surface 216 that, in exemplary form, is planar. A series of holes 220-224 extend through the femoral bone base plate 200 from the bone contacting surface 214 to the stem interfacing surface 216. In this exemplary embodiment, the femoral bone base plate 200 includes three holes 220 configured to receive screw fasteners (not shown) to mount the base plate 200 to the femur 204. In exemplary fashion, each hole 220 includes a recessed collar 226 that is operative to change the cylindrical diameter of each hole so that the hole at the stem interfacing surface 216 has a larger diameter than the hole at the bone contacting surface 214. Two additional holes 222 are provided that receive alignment studs associated with the stem 206. A fastener hole 224 is also provided, which may include helical threads, that is configured to receive a fastener in order to retain the femoral bone base plate into engagement with the stem 206.

Referring to FIGS. 14-19, the exemplary stem 206 includes a distal adapter 230 having a pair of alignment studs 232 extending therefrom that are configured to be received within respective holes 222 of the femoral bone base plate 200. In exemplary form, each alignment stud 232 comprises a linear, cylindrical shape that is received within a cylindrical bore of the respective holes 222. At the same time, the distal adapter 230 includes a through hole 234 of its own that is configured to receive a fastener 250 (such as the locking screw of FIG. 18, which may be threaded 252) to mount the distal adapter to the femoral bone base plate 200. In this exemplary embodiment, the distal adapter 230 includes a series of interconnected arcuate cut-outs 236 that unobstruct the holes 220 of the femoral bone base plate 200. Extending proximally from the distal adapter 230 is an elongated neck 240 terminating at a proximal coupling 242 configured to engage the IMU 202. The stem 206 is angled in three dimensions so that it can extend through a typical anterior THA incision before and after external rotation of the femur. The stem 206 has two configurations to accept the IMU 202. The first configuration of the stem 206 features a coupling 242 to accept the locking feature of the IMU 202. The second configuration of the stem 206 features a slide on which an IMU 202 is mounted.

Figure 20:
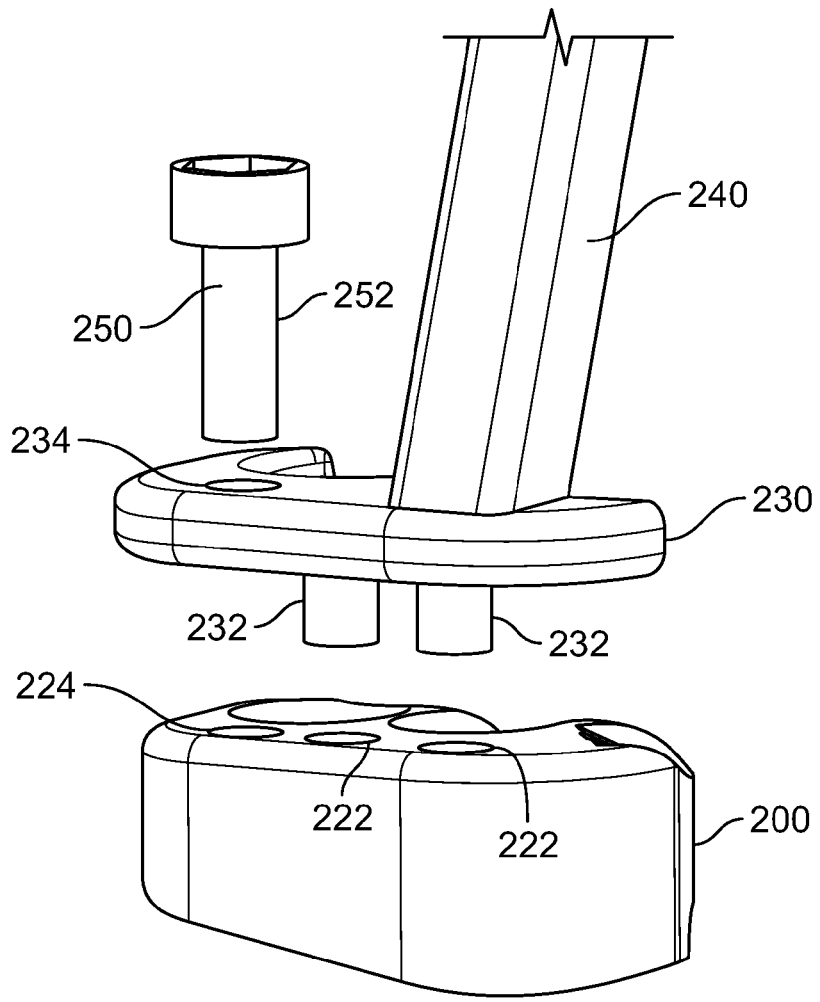
FIG. 20 is a partial exploded view showing the fastener, femoral base plate, and a portion of the stem prior to assembling them as a single element of the first exemplary bone reference assembly.
Figure 21:
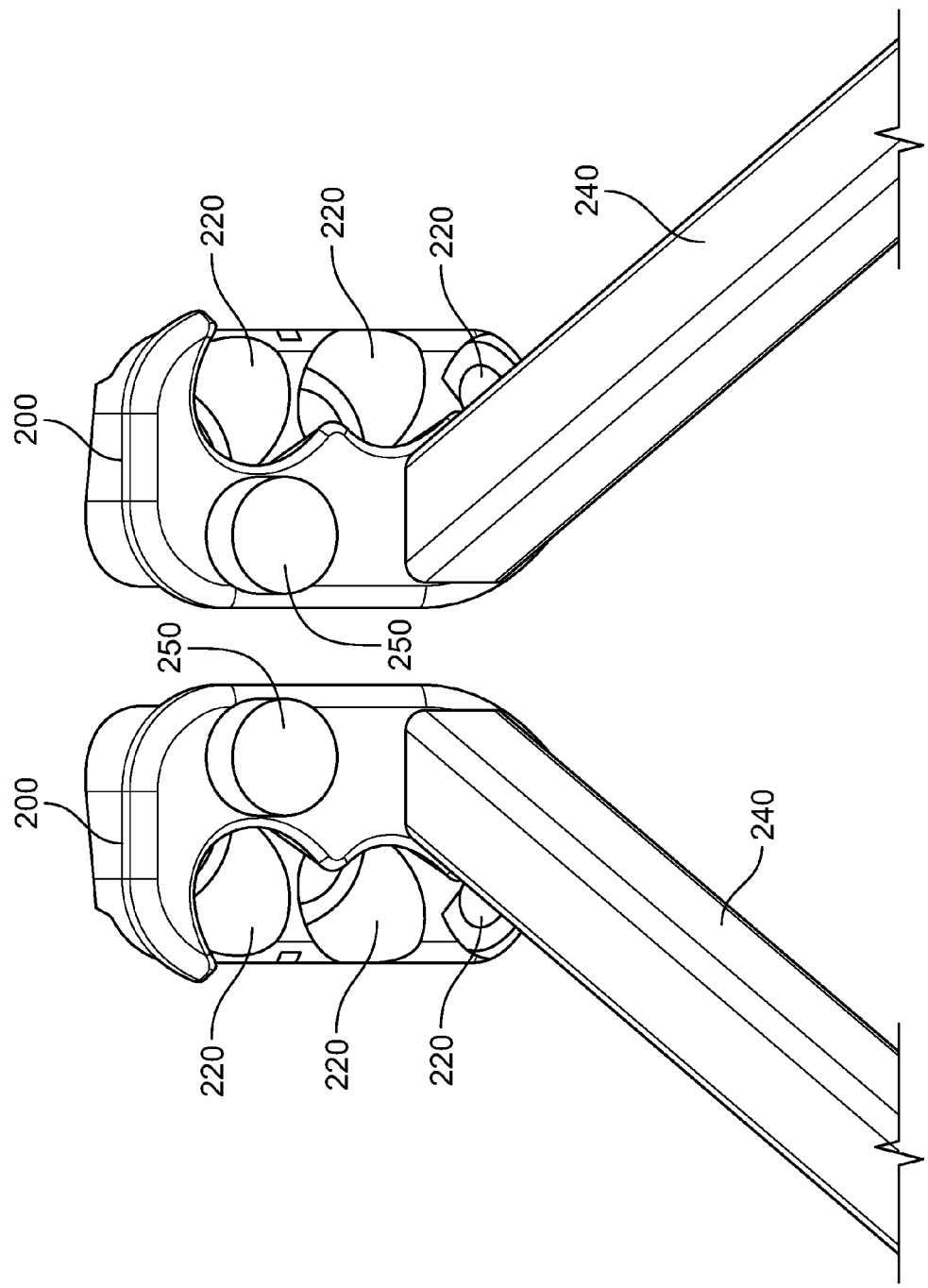
FIG. 21 is a left and right elevated perspective view of the components of FIG. 20 post assembly.

Referring to FIGS. 20 and 21, attachment of the stem 206 to the femoral bone base plate 200 includes aligning the studs 232 of the stem with the respective holes 222 of the base plate. By way of example, the studs 232 are designed to fit snugly with respect to the hole 222 boundaries to avoid significant play between the stem 206 and base plate 200. After the studs 232 are received within the holes 222, the through hole 234 of the adapter 230 should be aligned with the hole 224 of the base plate 200 so that the fastener 250 can extend through the smooth bore hole 234 and its threads 252 can engage the protruding threads of the hole 224. In this fashion, as the fastener 250 is rotated clockwise, the head of the fastener is operative to sandwich the adapter 230 in between the base plate 200. Upon proper torquing of the fastener 250, the stem 206 and the base plate 200 are fixedly mounted to one another. After being mounted to one another, the holes 222 of the base plate are available to be accessed by a drill and thereafter by a screw to mount the assembly 210 to the femur 204, presuming the IMU 202 is mounted to the stem 206.

When mounting the assembly 210 to a femur, the assembly is placed on the anterior of the proximal femur along the intertrochanteric line and perpendicular to the femoral neck axis during anterior total hip arthroplasty. It may be secured to the anterior femur with three 3.5 millimeter×20 millimeter cancellous screws (not shown). In this fashion, the reference IMU 202 is securely fixed to the patient femur.

Figures 22, 23:
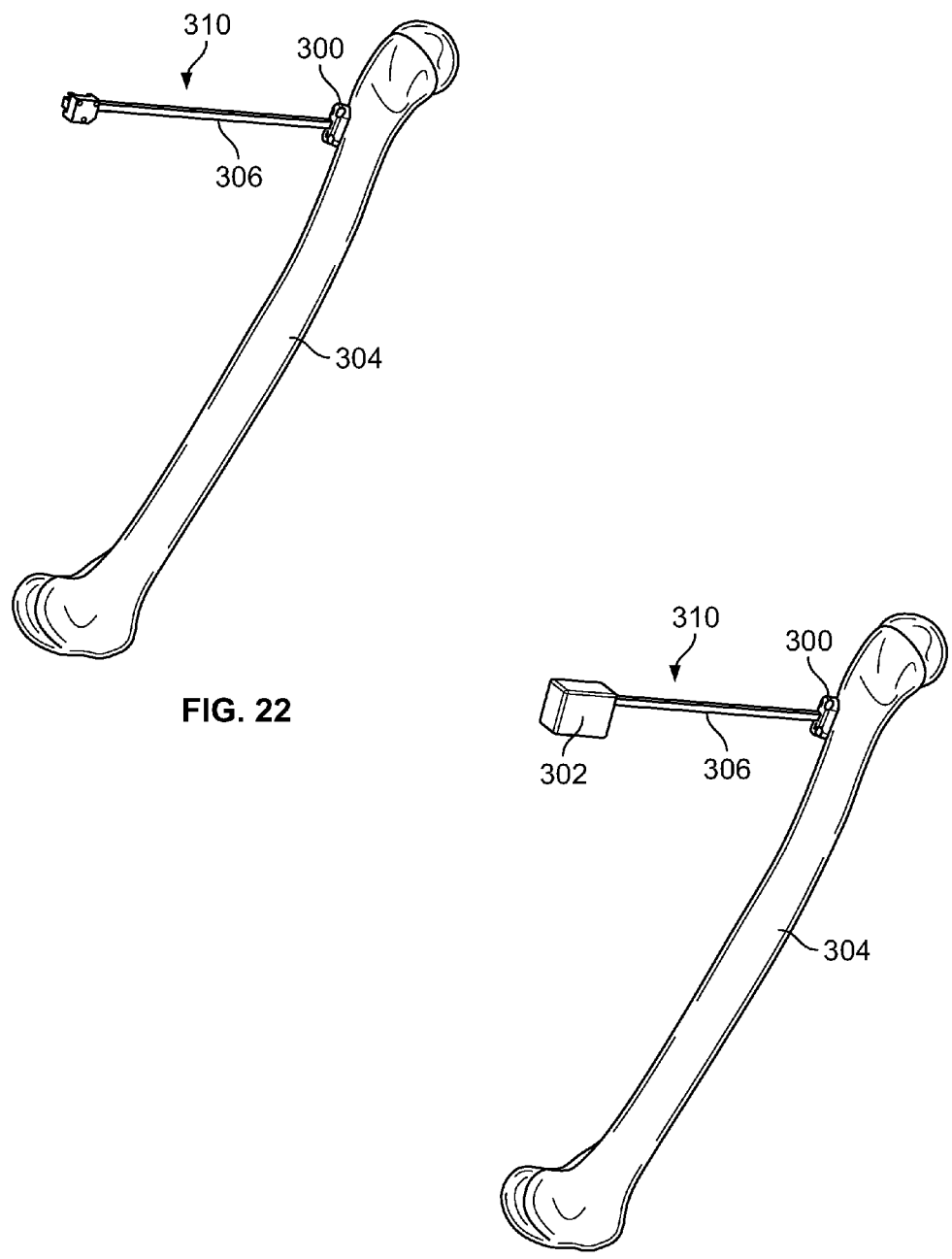
FIG. 22 is a diagram showing placement of the second exemplary bone reference assembly (without the IMU) on a posterior portion of a femur.
FIG. 23 is a diagram showing placement of the second exemplary bone reference assembly on a posterior portion of a femur.

Referring to FIGS. 22 and 23, an alternate exemplary embodiment of a bone reference assembly 310 for a femur 304 comprises an inertial measurement unit 302, a stem 306, and a bone base plate 300 (in exemplary form, a femoral bone base plate). Though not necessarily limited to applications on an attachment site on the posterior region of the femur, the foregoing exemplary embodiment may be referred to as an exemplary posterior bone reference assembly 310.

Figure 24:
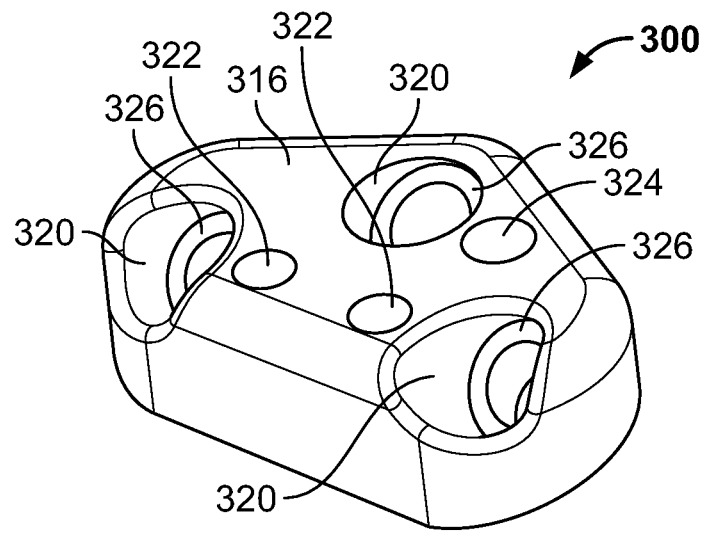
FIG. 24 is a top, elevated perspective view of a second exemplary femoral bone base plate in accordance with the instant disclosure.
Figure 25:
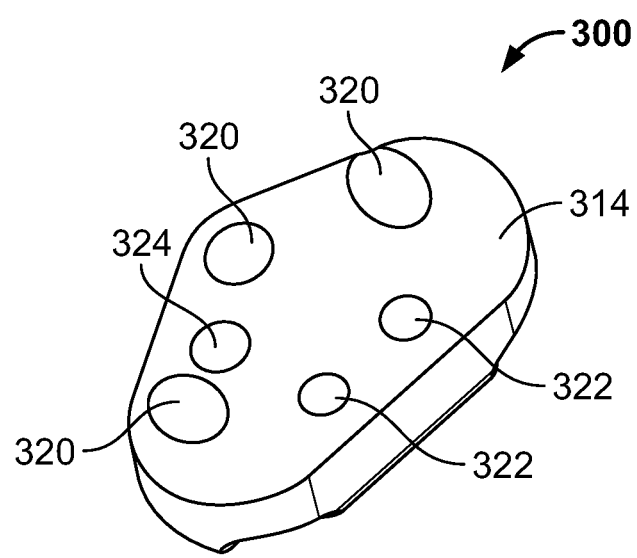
FIG. 25 is a bottom, subverted perspective view of the exemplary femoral base plate of FIG. 24.

As depicted in more detail in FIGS. 24-26, the shape of the exemplary femoral bone base plate 300 and fixation locations are established mathematically and confirmed using bone models 100 from a statistical atlas. The exemplary femoral bone base plate 300 includes a distal, bone contacting surface 314 having a topography that generally matches and mates with the topography of a posterior portion of a femur that is exposed as part of a total hip arthroplasty procedure. Opposite the bone contacting surface 314 is a stem interfacing surface 316 that, in exemplary form, is planar. A series of holes 320-324 extend through the femoral bone base plate 300 from the bone contacting surface 314 to the stem interfacing surface 316. In this exemplary embodiment, the femoral bone base plate 300 includes three holes 320 configured to receive screw fasteners (not shown) to mount the base plate 300 to the femur 304. In exemplary fashion, each hole 320 includes a recessed collar 326 that is operative to change the cylindrical diameter of each hole so that the hole at the stem interfacing surface 316 has a larger diameter than the hole at the bone contacting surface 314. Two additional holes 322 are provided that receive alignment studs associated with the stem 306. A fastener hole 324 is also provided, which may include helical threads, that is configured to receive a fastener in order to retain the femoral bone base plate into engagement with the stem 306.

Figure 29:
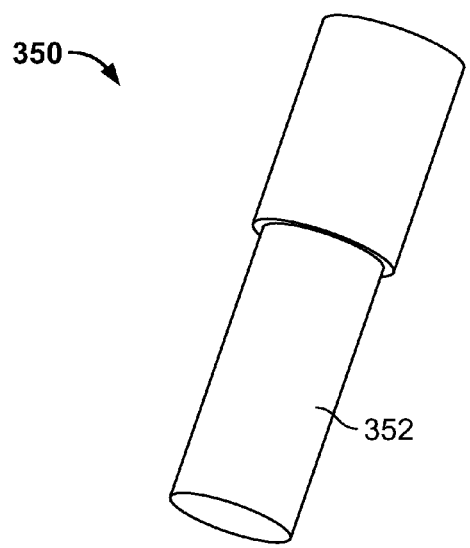
FIG. 29 is an elevated perspective view of a fastener in accordance with the instant disclosure.
Figure 30:
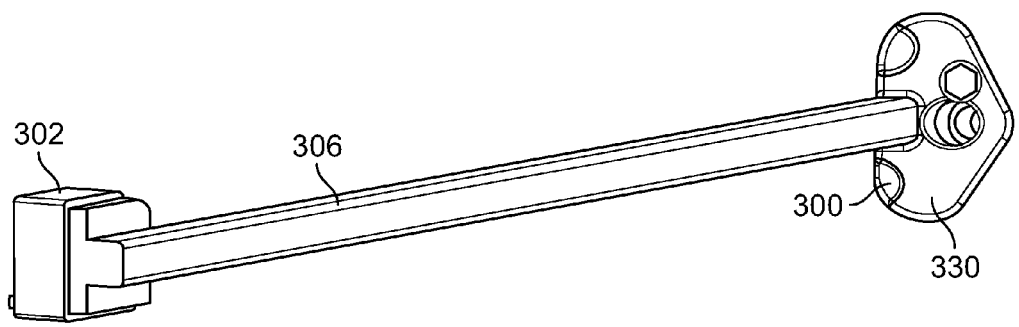
FIG. 30 is a left elevated perspective view of the components of the second exemplary bone reference assembly.
Figure 31:
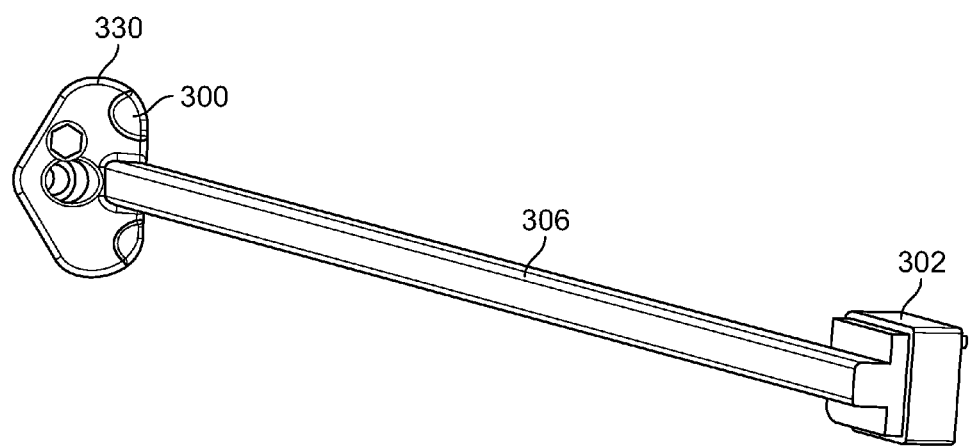
FIG. 31 is a right elevated perspective view of the components of the second exemplary bone reference assembly.
Figure 32:
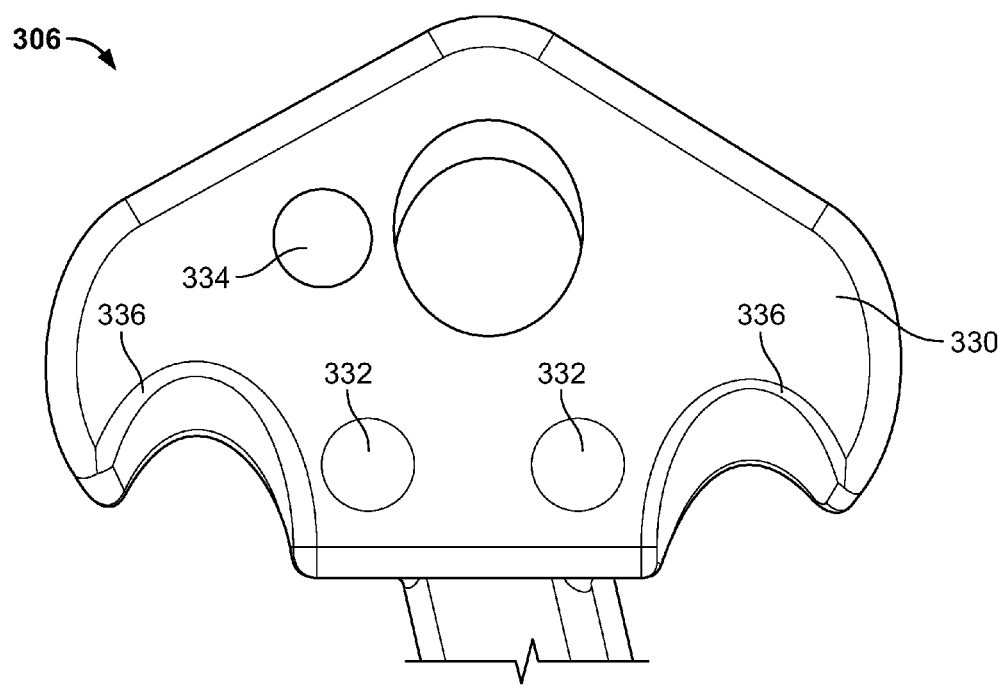
FIG. 32 is a bottom view of a portion of the second exemplary stem of FIG. 27.
Figure 33:
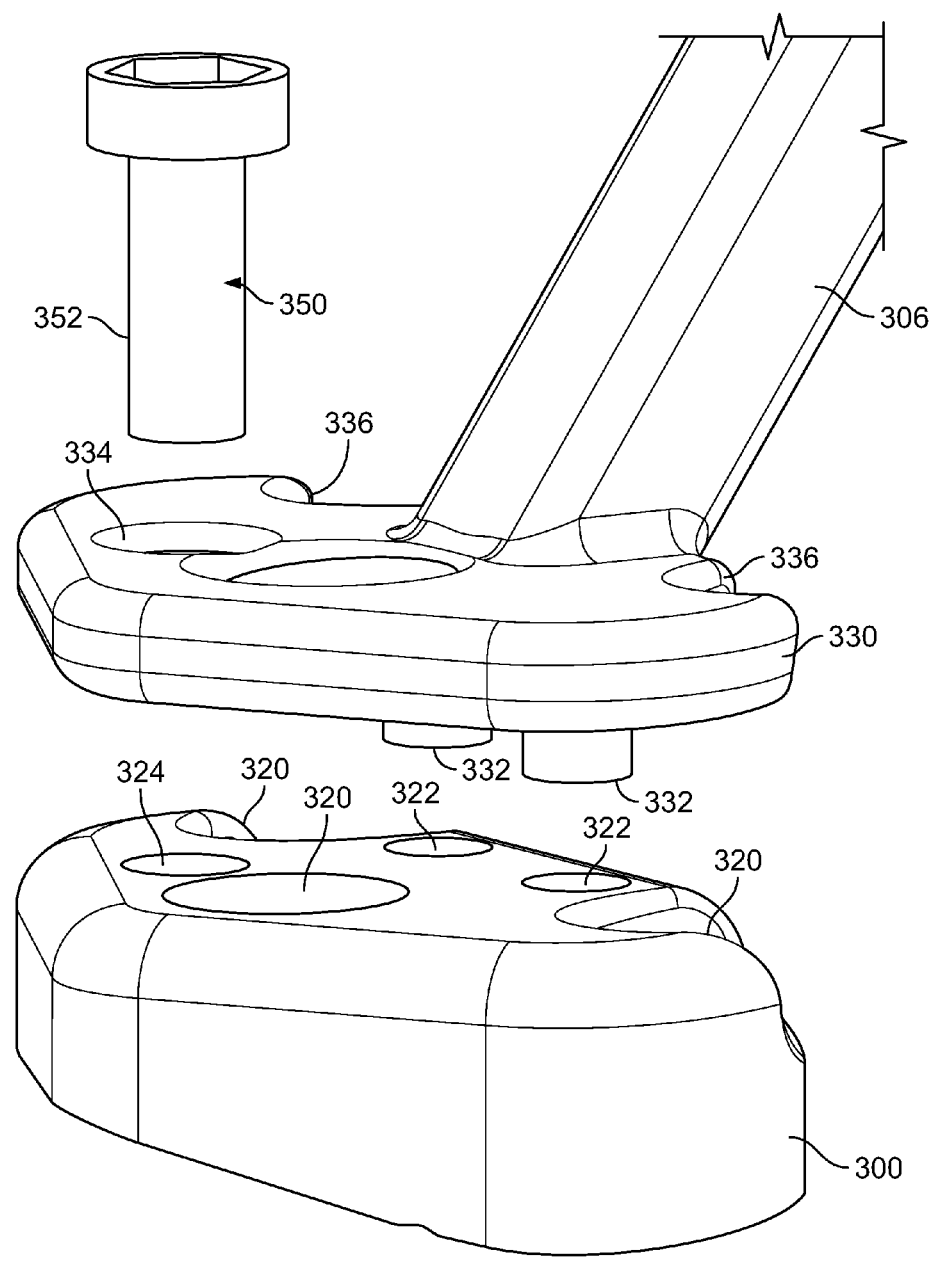
FIG. 33 is a partial exploded view showing the fastener, femoral base plate, and a portion of the stem prior to assembling them as a single element of the second exemplary bone reference assembly.

Referring to FIGS. 27 and 28, the exemplary stem 306 includes a distal adapter 330 having a pair of alignment studs 332 extending therefrom that are configured to be received within respective holes 322 of the femoral bone base plate 300. In exemplary form, each alignment stud 332 comprises a linear, cylindrical shape that is received within a cylindrical bore of the respective holes 322. At the same time, the distal adapter 330 includes a through hole 334 of its own that is configured to receive a fastener 350 (such as the locking screw of FIG. 29, which may be threaded 352) to mount the distal adapter to the femoral bone base plate 300. In this exemplary embodiment, the distal adapter 330 includes a pair of arcuate cut-outs 336 that unobstruct the holes 320 of the femoral bone base plate 300. Extending proximally from the distal adapter 330 is an elongated neck 340 terminating at a proximal coupling 342 configured to engage the IMU 302. The stem 306 is angled in three dimensions so that it can extend through a typical posterior THA incision before and after external rotation of the femur. The stem 306 has two configurations to accept the IMU 302. The first configuration of the stem 306 features a coupling 342 to accept the locking feature of the IMU 302. The second configuration of the stem 306 features a slide on which an IMU 302 is mounted.

Referring to FIGS. 30-33, attachment of the stem 306 to the femoral bone base plate 300 includes aligning the studs 332 of the stem with the respective holes 322 of the base plate. By way of example, the studs 332 are designed to fit snugly with respect to the hole 322 boundaries to avoid significant play between the stem 306 and base plate 300. After the studs 332 are received within the holes 322, the through hole 334 of the adapter 330 should be aligned with the hole 324 of the base plate 300 so that the fastener 350 can extend through the smooth bore hole 334 and its threads 352 can engage the protruding threads of the hole 324. In this fashion, as the fastener 350 is rotated clockwise, the head of the fastener is operative to sandwich the adapter 330 in between the base plate 300. Upon proper torquing of the fastener 350, the stem 306 and the base plate 300 are fixedly mounted to one another. After being mounted to one another, the holes 322 of the base plate are available to be accessed by a drill and thereafter by a screw to mount the assembly 310 to the femur 304, presuming the IMU 302 is mounted to the stem 306.

When mounting the assembly 310 to a femur, the assembly is placed on the posterior of the proximal femur along the intertrochanteric line and perpendicular to the femoral neck axis during posterior total hip arthroplasty. It may be secured to the posterior femur with three 3.5 millimeter×20 millimeter cancellous screws (not shown). In this fashion, the reference IMU 302 is securely fixed to the patient femur.

Following from the above description, it should be apparent to those of ordinary skill in the art that, while the methods and apparatuses herein described constitute exemplary embodiments of the present disclosure, the invention is not limited to these precise embodiments and that changes may be made to such embodiments without departing from the scope of the invention as defined by the claims. Additionally, it is to be understood that the invention is defined by the claims and it is not intended that any limitations or elements describing the exemplary embodiments set forth herein are to be incorporated into the interpretation of any claim element unless such limitation or element is explicitly stated. Likewise, it is to be understood that it is not necessary to meet any or all of the identified advantages or objects of the invention disclosed herein in order to fall within the scope of any claims, since the invention is defined by the claims and since inherent and/or unforeseen advantages of the present invention may exist even though they may not have been explicitly discussed herein.

What is claimed is:

1. A method of creating a mass-customized femoral bone base plate comprising:
    establishing anatomical landmarks across a plurality of bone models of a statistical atlas;
    establishing instrument landmarks across the plurality of bone models of the statistical atlas;
    establishing definitions for a reference plane calculation across the plurality of bone models of the statistical atlas, where the reference plane represents a boundary of a prosthetic implant;
    establishing an attachment site for a mass-customized femoral bone base plate using the anatomical landmarks, the instrument landmarks, and the reference plane; and,
    fabricating the mass-customized femoral bone base plate configured to be attached to a femur, where the attachment sites of the mass-customized femoral bone base plate are predetermined to avoid impingement with the prosthetic implant when implanted.

2. The method of claim 1, wherein establishing the anatomical landmarks includes computing a tip of a femoral lesser trochanter point for each of the plurality of bone models of the statistical atlas.

3. The method of claim 1, wherein establishing the anatomical landmarks includes computing a plane marking an edge of a lesser trochanter, tangent to a femoral shaft for each of the plurality of bone models of the statistical atlas.

4. The method of claim 1, wherein establishing the anatomical landmarks includes computing a femoral overall anatomical axis for each of the plurality of bone models of the statistical atlas.

5. The method of claim 1, wherein establishing the anatomical landmarks includes computing a projection of a lesser trochanter point on a femoral overall anatomical axis for each of the plurality of bone models of the statistical atlas.

6. The method of claim 1, wherein establishing the anatomical landmarks includes computing a projection of a lesser trochanter point on a plane marking an edge of a lesser trochanter for each of the plurality of bone models of the statistical atlas.

7. The method of claim 1, wherein establishing the anatomical landmarks includes computing a medial-lateral direction as a vector between a projection of a lesser trochanter point on a femoral overall anatomical axis and the femoral lesser trochanter point for each of the plurality of bone models of the statistical atlas.

8. The method of claim 1, wherein establishing the anatomical landmarks includes computing an anterior-posterior direction as a cross product of a femoral overall anatomical axis and a medial-lateral direction for each of the plurality of bone models of the statistical atlas.

9. The method of claim 1, wherein establishing the anatomical landmarks includes computing a superior inferior direction as a femoral overall anatomical axis direction for each of the plurality of bone models of the statistical atlas.

10. The method of claim 1, wherein establishing the instrument landmarks includes computing a shifted lesser trochanter point as a projection of the lesser trochanter point on a plane marking an edge of the lesser trochanter is shifted 1 millimeter in a medial-lateral direction for each of the plurality of bone models of the statistical atlas.

11. The method of claim 10, wherein establishing the instrument landmarks includes computing a location of a fastener for the mass-customized femoral bone base plate as an intersection of a line pointing along an anterior-posterior direction and passing through the shifted lesser trochanter point for each of the plurality of bone models of the statistical atlas.

12. The method of claim 1, wherein establishing the instrument landmarks includes computing a midpoint between two fasteners for the mass-customized femoral bone base plate to establish a location of a third fastener shifted between zero and ten millimeters in a medial-lateral direction for each of the plurality of bone models of the statistical atlas.

13. The method of claim 1, wherein establishing the instrument landmarks includes computing a location for a fastener for the mass-customized femoral bone base plate that is a closest point on a femoral bone model to a shifted lesser trochanter point for each of the plurality of bone models of the statistical atlas.

14. The method of claim 1, wherein establishing the instrument landmarks includes computing a location of a fastener for the mass-customized femoral bone base plate that is shifted distally in a direction of an anatomical axis for each of the plurality of bone models of the statistical atlas.

15. The method of claim 1, wherein establishing the instrument landmarks includes computing a femoral plate plane as the plane containing at least one fastener location for the mass-customized femoral bone base plate for each of the plurality of bone models of the statistical atlas.

16. The method of claim 1, wherein establishing the instrument landmarks includes computing a direction of a fastener for the mass-customized femoral bone base plate for each of the plurality of bone models of the statistical atlas.

17. The method of claim 16, wherein the direction is taken normal to a femoral plate plane.

18. The method of claim 17, wherein the femoral plate plane is rotated between ten and thirty degrees medially around an axis connecting the location of multiple fasteners for the mass-customized femoral bone base plate.

19. The method of claim 1, wherein establishing the definitions includes defining a reference plane normal to a proximal anatomical axis and a neck axis and passing through an anatomical axis point for each of the plurality of bone models of the statistical atlas.

20. The method of claim 1, wherein establishing the definitions includes computing a reference plane as a plane rotated between zero and ten degrees and translated between zero and 15 millimeters for each of the plurality of bone models of the statistical atlas.

* * * * *